United States Patent
O'Donnell, Jr.

[19]

[11] Patent Number: 6,086,602
[45] Date of Patent: *Jul. 11, 2000

[54] APPARATUS AND METHOD FOR ASTIGMATICALLY-NEUTRAL WOUND CLOSURE

[76] Inventor: Francis E. O'Donnell, Jr., 709 The Hamptons La., Town & Country, Mo. 63017

[*] Notice: This patent is subject to a terminal disclaimer.

[21] Appl. No.: 09/122,971

[22] Filed: Jul. 27, 1998

Related U.S. Application Data

[60] Provisional application No. 60/053,994, Jul. 28, 1997.

[51] Int. Cl.⁷ ........................................... A61F 9/00
[52] U.S. Cl. ............................................... 606/166
[58] Field of Search ..................... 606/144–148, 606/166, 4, 5, 228; 128/898, 899

[56] References Cited

U.S. PATENT DOCUMENTS

| | | |
|---|---|---|
| 3,126,680 | 3/1964 | Baird, Jr. et al. . |
| 3,359,193 | 12/1967 | Pinner et al. . |
| 3,372,100 | 3/1968 | Charlesby et al. . |
| 4,596,720 | 6/1986 | Keryk et al. . |
| 5,090,425 | 2/1992 | Stahl . |
| 5,234,006 | 8/1993 | Eaton et al. . |
| 5,261,923 | 11/1993 | Soares ..................................... 606/166 |
| 5,308,355 | 5/1994 | Dybbs ..................................... 606/166 |
| 5,464,424 | 11/1995 | O'Donnell, Jr. . |
| 5,651,377 | 7/1997 | O'Donnell, Jr. . |
| 5,860,994 | 1/1999 | Yaacobi ................................... 606/166 |

Primary Examiner—Michael Buiz
Assistant Examiner—Vikki Trinh
Attorney, Agent, or Firm—Paul M. Denk

[57] ABSTRACT

Astigmatically-neutral wound closure is achieved by creation of a precisely-sized keratotomy anterior to a wound. Through the posterior wall of the keratotomy is passed a radial suture element. Increased tension in the suture element causes posterior gaping of the keratotomy, reducing unwanted distortion of the cornea anterior to the keratotomy.

4 Claims, 4 Drawing Sheets

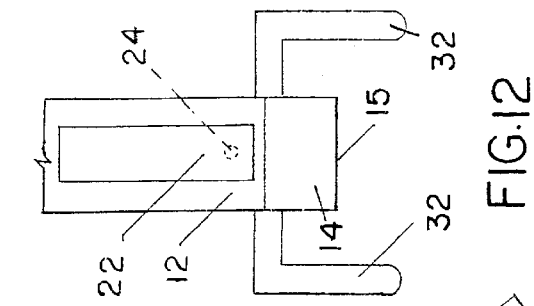
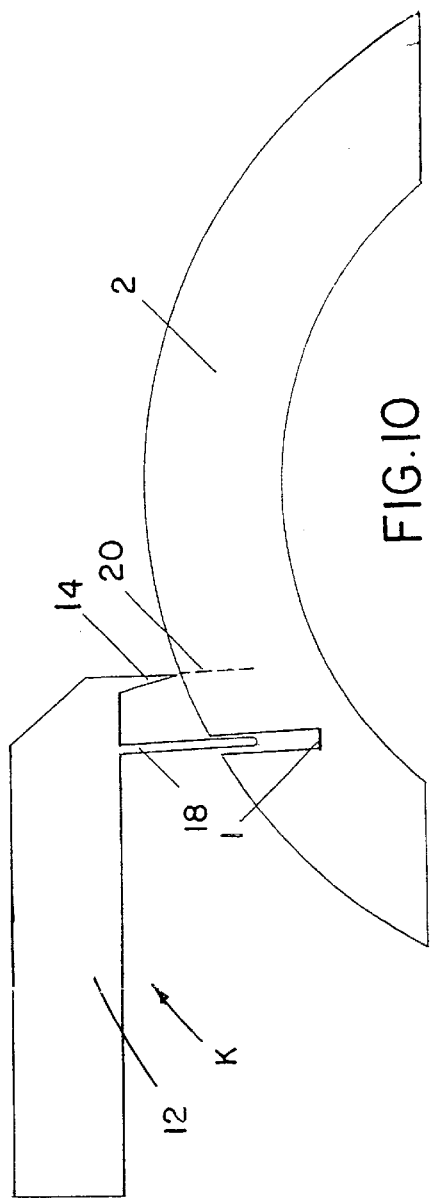
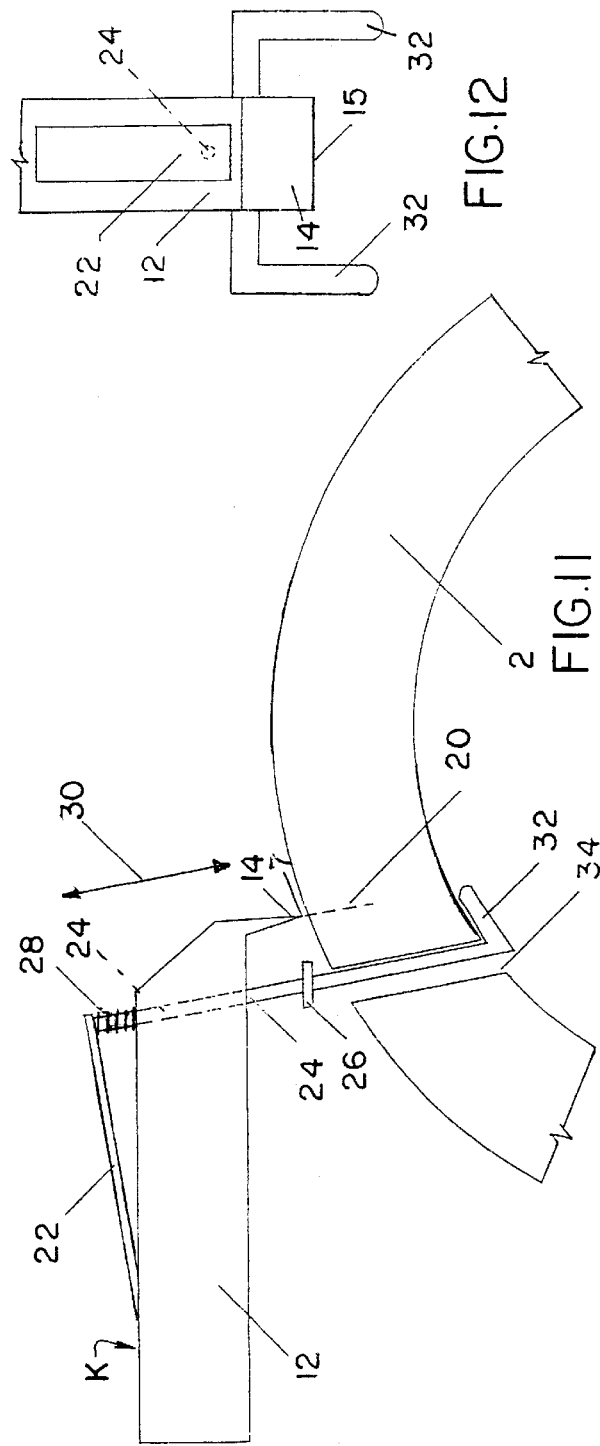

APPARATUS AND METHOD FOR ASTIGMATICALLY-NEUTRAL WOUND CLOSURE

This Application claims benefit of provisional Application 60/053,994 Jul. 28, 1997.

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to a device and method for closure of ocular wounds, more particularly, closure of ocular wounds (surgical or traumatic) in order to make a watertight compression of the wound by a suture. The present invention allows for suture closure of ophthalmic wounds without creation of astigmatism (unwanted distortion of the cornea).

Prior art has been unable to eliminate induced astigmatism from suture closure of ocular wounds, whether surgical or traumatic. Alternative approaches to surgical wound closure for cataract operation, for example, have attempted to eliminate suturing in order to eliminate unwanted induced astigmatism. Such wounds are generally small (2–5 mm) and stepped so as to be self-sealing.

The present invention uses a novel means to eliminate induced astigmatism from suture closure of ophthalmic wounds. For ophthalmic surgery, this means the ability to use larger wound dimensions which permit safer and technically less demanding delicate eye surgery such as extracapsular cataract extraction with intraocular implant insertion. In the cases of corneal transplant surgery, the present invention eliminates the heretofore unavoidable delay in recovery of vision due to high astigmatism. For management of ocular injuries such as corneal lacerations, it means the ability to achieve a watertight closure without inducing unwanted astigmatism (distortion of the central cornea). In order to facilitate the placement of the keratotomy incision in an atraumatic manner, a novel ultrasonic keratotomy knife is used.

BRIEF SUMMARY OF THE INVENTION

The object of the present invention is to provide a device and method which permits watertight closure of ocular wounds, and more specifically, limbal and corneal wounds without inducing unwanted distortion of the control cornea (astigmatism).

Another object of the present invention is to allow the use of astigmatically-neutral larger wounds for extracapsular cataract extraction, giving enhanced safety and reduced dependence on costly, complicated phacoemulsification machines that are used for self-sealting, small incision, astigmatically-neutral cataract surgery.

Another object of this invention is to allow for astigmatically-neutral penetrating keratoplasty (corneal transplant surgery). By eliminating high astigmatism post-keratoplasty, the present invention provides significantly better visual results for corneal transplant patients.

Still another object of this invention is the repair of corneal lacerations in an astigmatically7-neutral fashion. For this purpose, centrally located corneal lacerations may require the keratotomy of the present invention, on both sides of the ocular wound.

(1) The limbal cataract wound incision;
(2) The corneal limbus;
(3) The keratotomics of the present invention;
(4) Pupil;
(5) Iris.

Figure 2:
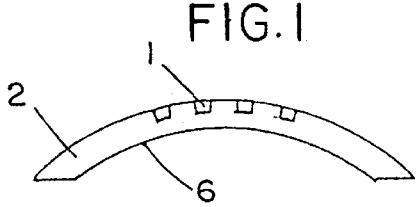

FIG. 2 is a schematic of the keratotomy wound of the present invention;

(1) Keratotomy demonstrating a partial-thickness depth;
(2) Cornea;
(6) Posterior cornea (endothelial cell layer).

Figure 1:
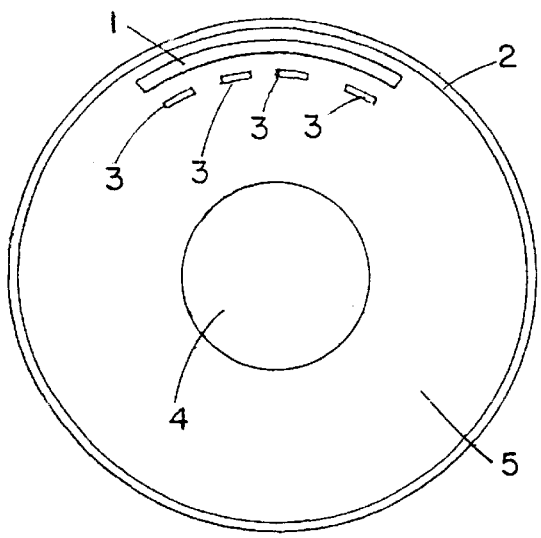
FIG. 1 is a schematic of the keratotomy wound of the present inveniton.
Figure 3:
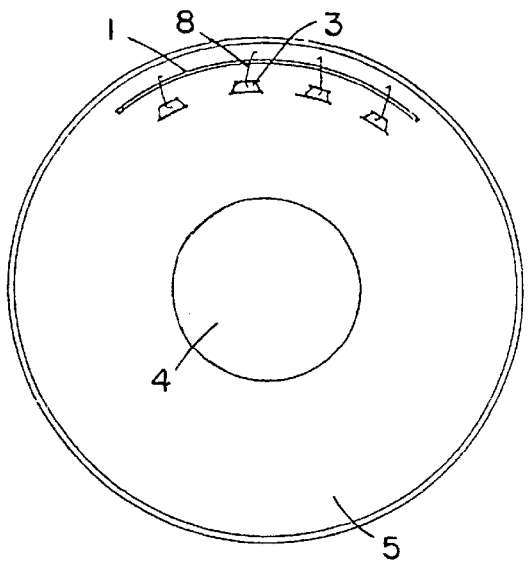

FIG. 3 is the schematic of the present invention demonstrating the placement of the sutures (8) to close the cataract wound (W) with the suture passing through the posterior lip of the keratotomy (13) of the present invention (10).

Figure 4:
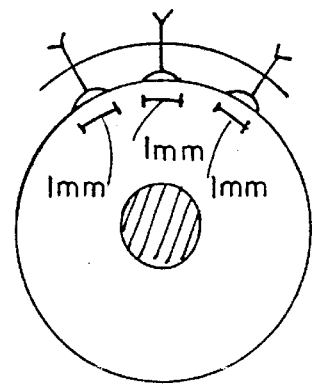

FIG. 4 shows a videokeratographic topography map of an eye bank eye in which the preferred embodiment illustrated in FIG. 3 was used to close a simulated surgical limbal wound. The pre-wound topography is shown on the upper left-hand side. The post-wound closure topography using the present invention is shown on the lower left-hand side. The subtraction map on the right-hand side discloses no significant induced astigmatism.

Figure 5:
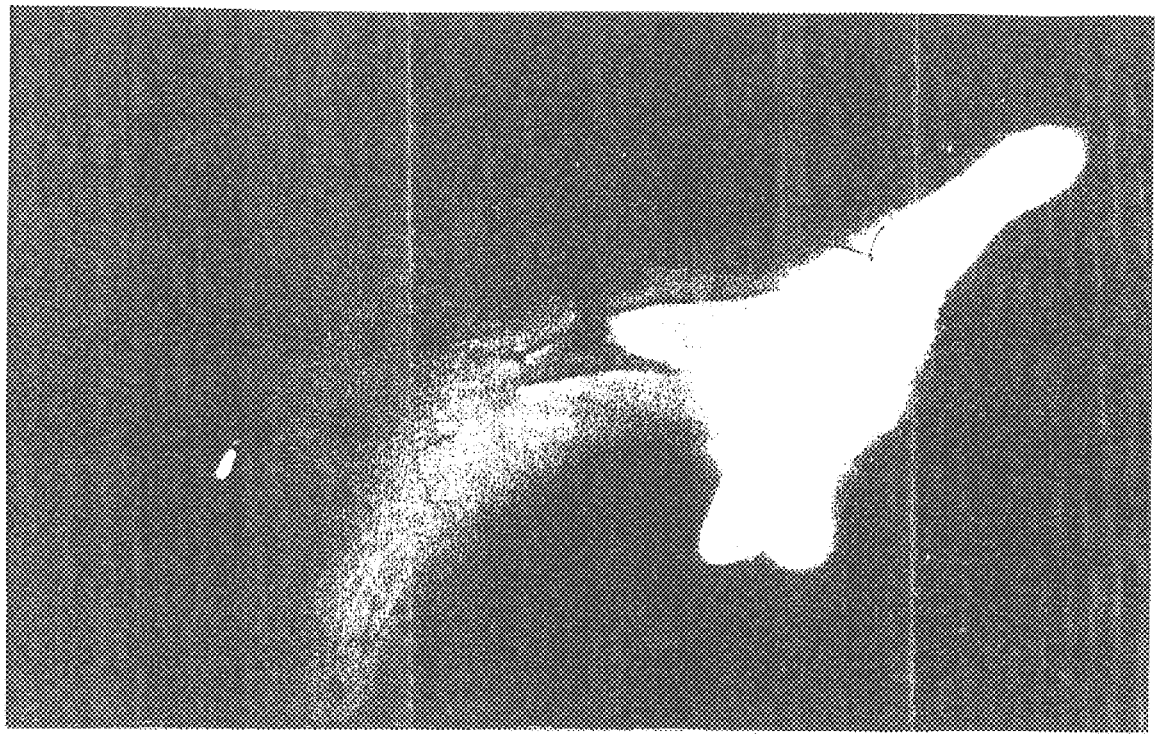

FIG. 5 is an eye bank eye demonstrating the present invention. A black radial suture is visible, closing the simulated cataract wound and stretching the posterior lip of the keratotomy.

Figure 6:
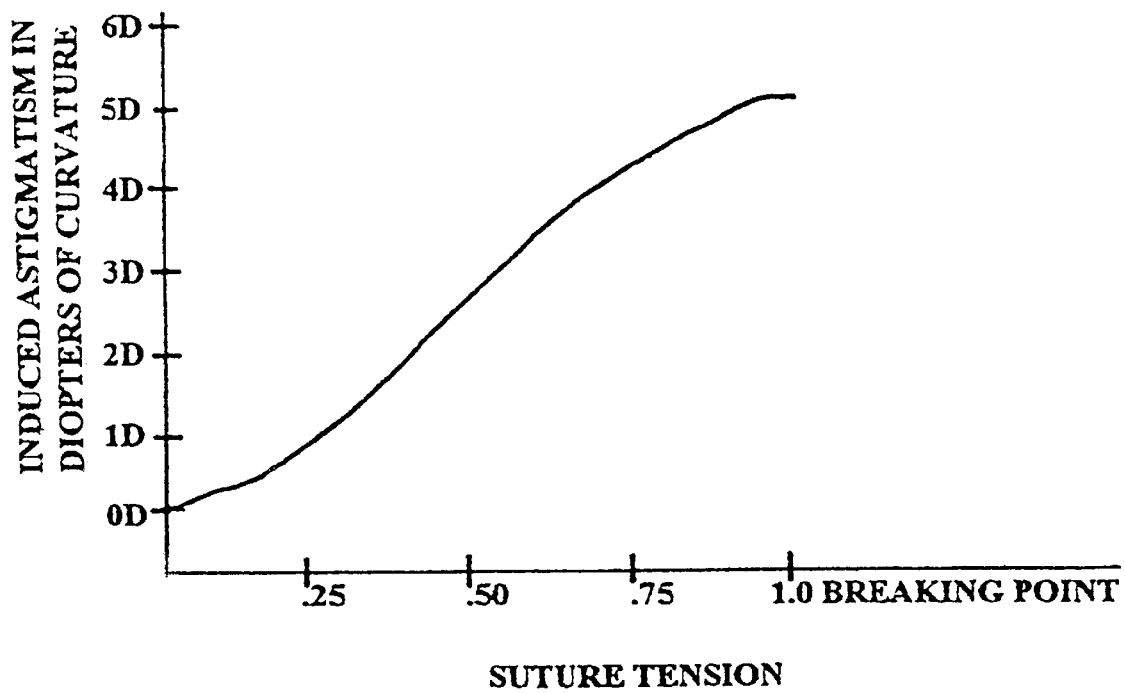

FIG. 6 is a plot of induced astigmatism as tensile strength on a radial suture increases to a nominal maximum (1.0) at which point the suture material (10-0 nylon)_ breaks, using standard wound closure technique.

Figure 7:
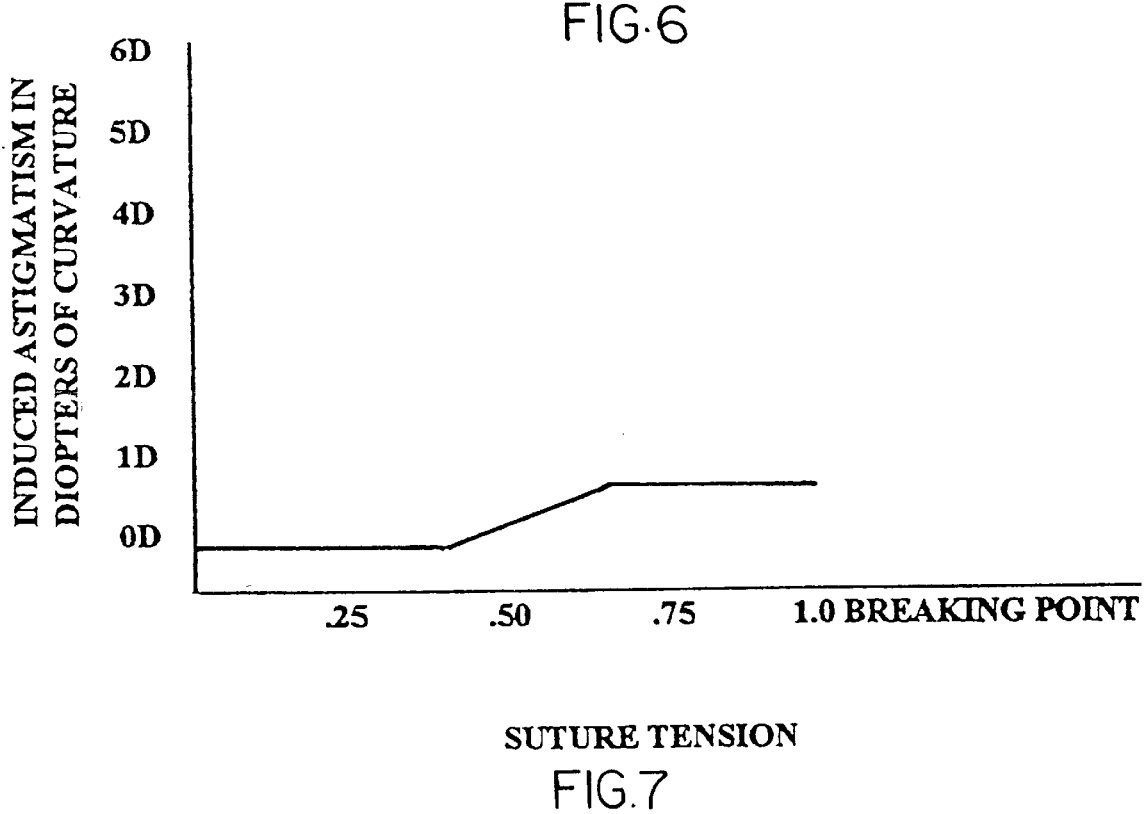

FIG. 7 is a plot of induced astigmatism as tensile strength on a radial sut6ure; increases to a nominal maximum (1.0) at which point the suture material (10.0) nylon breaks, using the present invention.

Figure 8B:
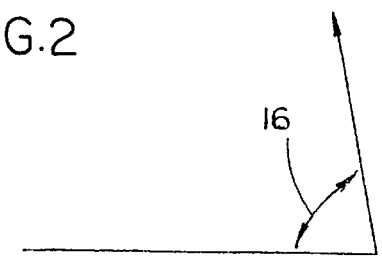
Figure 8A:
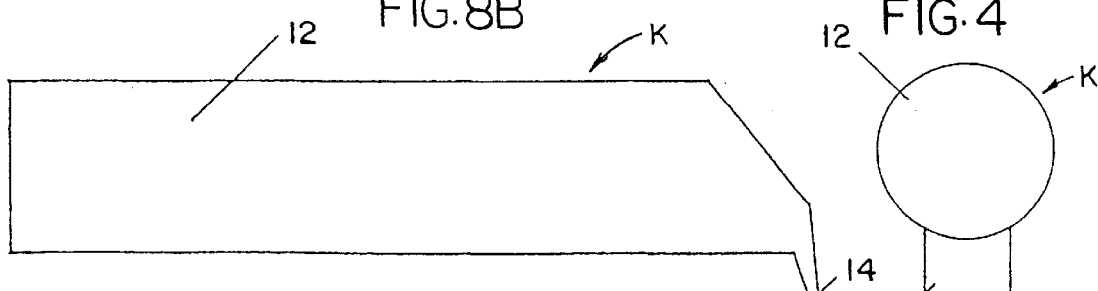

FIG. 8A is a side view of the blade of the present invention:

(1) Handle of the blade;
(2) The cutting blade itself;
(3) The angle of the blade to the handle.

Figure 9:
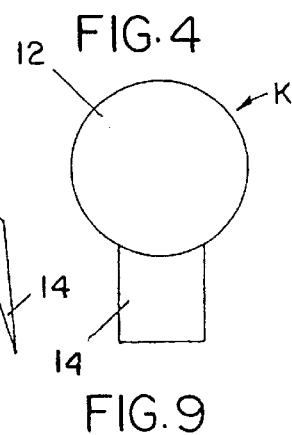

FIG. 8B illustrates the angle of the cutting blade (14) to the handle (12);

FIG. 9 is a frontal view of FIG. 8A. It demonstrates a frontal view of the horizontal element of the blade and the cutting blade (14) itself on a frontal view.

FIG. 10 shows the knife of the present invention for making the keratotomy of a predetermined width and depth, and displacement from the ocular wound to be sutured closed. In this case, the present invention is used to create a keratotomy before a full-thickness wound is established. The knife handle (12) has a distance guide (18) which is inserted into the partial-thickness wound (3) of the cornea (2). The cutting blade (14) can be attached to an ultrasonic source (1) in order to facilitate the cutting action of the blade (5).

FIG. 11 shows the knife of the present invention for making the keratotomy of a predetermined width and depth, and displacement from the ocular wound to be sutured closed. In this case, the present invention is used to create a keratotomy after a full-thickness wound (34) has been created. Handle (12) has a spring-loaded engage/release element (22) for depressing the cutting edge of blade (14) into the cornea (2) at position (20). The distance (30) corresponds to the predetermined incision depth for creation of the keratotomy (3) by blade (14). A stop (26) can be used in conjunction with an I-shaped tissue supports or struts (32) to stabilize the cornea for creation of the keratototmy. Horizontal blade handle (12) can be attached to an ultrasonic device for facilitating the cutting action.

FIG. 12 is a top view of FIG. 11. It demonstrates the spring-loaded device (28) underlying the engage/release element (22) which is an extension off of the cutting blade elements (12). The exterior corneal stabilizing element (15) and the interior corneal stabilizing elements (32) are identified.

DETAILED DESCRIPTION OF THE INVENTION

In a preferred embodiment of the present invention, a keratotomy (3) of precisely determined width and depth is placed in a precisely determined location "anterior" (more central) to a surgical wound (1). The radial suture (8) used to compress the surgical wound (1) closed is inserted so that it passes through the posterior (more peripheral) lip of the keratotomy (3). Thus arranged, the suture tension can be increased in order to compress the surgical wound without distorting the central cornea (2).

In one preferred embodiment, the keratotomy (3) is placed 250 to 1,000 or so microns anterior to the surgical wound.

In another preferred embodiment, the keratotomy (3) is made to a precisely predetermined depth of 200 to 500 or so microns.

In another preferred embodiment, the keratotomy (3) is made to a precisely predetermined with of 0.5 mm to 1.5 mm or so.

In another preferred embodiment, the keratotomy (3) is made with a knife whose cutting blade (14) has dimensions according to the preferred dimensions of the keratotomy.

In another preferred embodiment, the keratotomy knife is attached to an ultrasonic source such as piezoelectric transducer in order to facilitate the cutting action of the keratotomy blade. The ultrasound is pulsed at 21 to 40 KHz.

In another preferred embodiment, the keratotomy knife (K) of the present invention has a member which is inserted into the ocular wound so as to place the keratatotmy incision (1) a precise distance from the wound (incision (1)). In the case of a full-thickness wound, such as a corneal laceration, the keratotomy knife member for wound insertion features short struts, or tissue supports (32) that are placed into contact with the endothelial surface in order to stabilize and support the cornea for placement of the keratotomy incisions of the present invention.

I claim:

1. A method of performing an astigmatically neutral suture closure of ocular wounds comprising the steps of:

creating a plurality of discreet keratotomies at a predetermined distance anteriorly to the ocular wound, said keratotomies are placed approximately 250 to 100 microns anterior to the ocular wound, and placing a suture through the posterior lip of each of the plurality of keratotomies for compression of the ocular wound.

2. The method of claim 1 wherein the keratotomies are approximately 0.5 mm to 1.5 mm in width.

3. The method of claim 1 wherein the keratotomies are approximately 200 to 500 microns in depth.

4. The method of claim 1 wherein the step of placing a suture through the posterior lip of the keratotomies further comprises placing a suture through each posterior lip of the keratotomies substantially vertical to the ocular wound.

* * * * *